US00PP16659P2

(12) United States Plant Patent
Lim

(10) Patent No.: US PP16,659 P2
(45) Date of Patent: Jun. 13, 2006

(54) SHRUB ROSE PLANT NAMED 'BAIINE'

(50) Latin Name: *Rosa hybrida*
Varietal Denomination: BAIine

(75) Inventor: Peter P. Lim, Yamhill, OR (US)

(73) Assignee: Bailey Nurseries, Inc., St. Paul, MN (US)

( * ) Notice: Subject to any disclaimer, the term of this patent is extended or adjusted under 35 U.S.C. 154(b) by 96 days.

(21) Appl. No.: 10/992,135

(22) Filed: Nov. 19, 2004

(51) Int. Cl.
*A01H 5/00* (2006.01)

(52) U.S. Cl. ..... Plt./104

(58) Field of Classification Search ..... Plt./104, Plt./145
See application file for complete search history.

*Primary Examiner*—Anne Marie Grunberg
*Assistant Examiner*—June Hwu
(74) *Attorney, Agent, or Firm*—Buchanan Ingersoll PC

(57) ABSTRACT

A new and distinct variety of landscape shrub rose plant is provided which abundantly forms on a recurrent basis in clusters attractive double lemon yellow blossoms that mature to pale yellow creating a blend of yellow tints. The blossoms also display a medium rose fragrance. The plant exhibits a dense upright and bushy growth habit, attractive semi-glossy medium green foliage, and good tolerance to Black Spot and Powdery Mildew. The attractive medium green semi-glossy foliage contrasts nicely with the medium yellow blossom coloration. The new variety is particularly well suited for growing as attractive ornamentation in parks and gardens. The plant is most attractive when planted in groups with other shrubs and perennials.

2 Drawing Sheets

Botanical commercial classification: *Rosa hybrida*/Shrub Rose Plant.
Varietal denomination: cv BAIine.

SUMMARY OF THE INVENTION

The new variety of *Rosa hybrida* landscape shrub rose plant was created at Yamhill, Oreg., U.S.A., during 1996 by artificial pollination wherein two parents were crossed which previously had been studied in the hope that they would contribute the desired characteristics. The female parent (i.e., the seed parent) was the 'MACivy' variety (U.S. Plant Pat. No. 8,362). The 'MACivy' variety sometimes is known as the 'Singin' in the Rain' variety. The male parent (i.e., the pollen parent) was an unreleased shrub rose from my breeding program designated R93412 (non-patented in the United States). The parentage of the new variety can be summarized as follows:

'MACivy'×'R93412'.

The seeds resulting from the above pollination were sown and plants were obtained which were physically and biologically different from each other. Selective study resulted in the identification during 2000 of a single plant of the new variety having the distinctive ornamental characteristics hereafter described.

It was found that the new variety of the present invention:

(a) exhibits a dense upright and bushy growth habit, (b) forms on a recurrent basis in clusters attractive double lemon yellow blossoms that mature to pale yellow creating a blend of yellow tints, (c) forms attractive semi-glossy medium green foliage, (d) is highly tolerant to Black Spot and Powdery Mildew; and (e) is particularly well suited for growing as attractive ornamentation in parks and gardens.

The deep yellow buds open to lemon yellow blossoms that age to pale yellow and finally to creamy white. Thereby a blend of yellow tints is created.

The new variety well meets the needs of the horticultural industry and can be grown to advantage in the landscape where attractive ornamentation is desired. The plant is most attractive when planted in groups with other shrubs and perennials. The medium yellow blossoms contrast nicely with the semi-glossy medium green foliage. An attractive tough new shrub rose that can be grown in U.S.D.A. Hardiness Zone Nos. 4 to 9 is provided.

The new variety can be readily distinguished from other varieties including its ancestors. For instance, the 'MACivy' variety is a Floribunda that forms apricot/copper blooms having approximately 25 to 30 petals, bears medium green to dark green glossy foliage, and displays a sweet musk fragrance. R93412 is a shrub rose that forms light yellow blossoms of approximately 15 petals having a diameter of approximately 8 cm, and forms glossy dark green foliage with red new growth.

Also, the new variety readily can be distinguished from the 'J. P.Connell' (U.S. Plant Pat. No. 6,793) and 'MORyelrug' (non-patented in the United States) varieties. More specifically, the 'J. P.Connell' variety exhibits a generally taller growth habit and forms considerably larger blossoms having a lesser number of petals, and the 'MORyelrug' variety is a hybrid Rugosa that also forms considerably larger blossoms having a lesser number of petals.

The new variety beginning in August 1997 has been found to undergo asexual propagation by budding on an understock and by the rooting of cuttings. 'Dr. Huey' rootstock was used during the budding. Such asexual propagation by these techniques at Yamhill, Oreg., U.S.A., St. Paul, Minn., U.S.A., and at Phoenix, Ariz., U.S.A. has shown that the characteristics of the new variety are stable and are strictly transmissible by such asexual propagation from one generation to another. Accordingly, the new variety reproduces true to type. The new variety grows well on its own roots.

Initially the new plant was designated 96R683. The new plant has been named the 'BAIine' variety, and currently is being marketed while using the GARDEN ART, EASY ELEGANCE, and YELLOW SUBMARINE trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately two and three years of age, and were being grown outdoors during the 2003 and 2004 seasons at St. Paul, Minn., U.S.A., and at Yamhill, Oreg., U.S.A.

DETAILED DESCRIPTION

The chart used in the identification of the colors is that of The Royal Horticultural Society (R.H.S. Colour Chart). Common color terms are to be accorded their ordinary dictionary significance. The description is based on the observation of two, and four year-old plants while grown outdoors on their own roots during June 2003, at Yamhill Oreg., U.S.A., and during July 2004 at St. Paul, Minn., U.S.A.

Botanical classification: *Rosa hybrida*, 'BAIine'.
Class: Landscape Shrub.
Plant:
- *Height*.—Approximately 60 cm to 1 m at the end of the growing season. The height is influenced by the length of the growing season.
- *Width*.—Approximately 80 cm to 1.25 m on average at the end of the growing season. The width is influenced by the length of the growing season.
- *Habit*.—Dense, upright and bushy.

Figure 1:
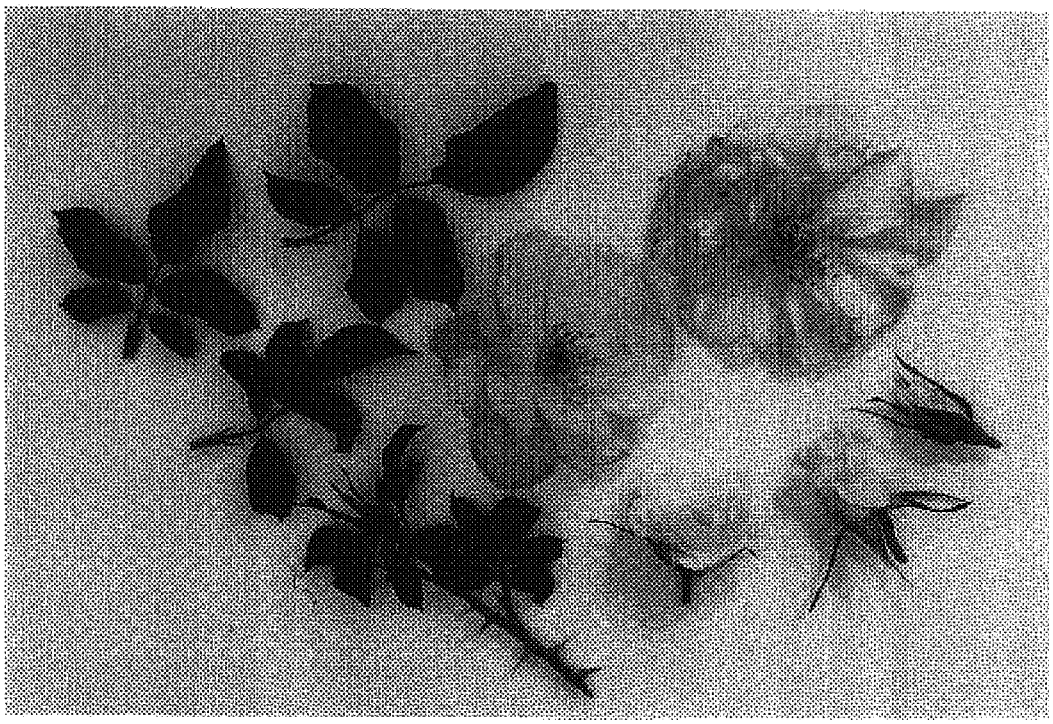
FIG. 1 illustrates at the right typical flowers in various stages of opening and at the left typical leaves and new growth.
Figure 2:
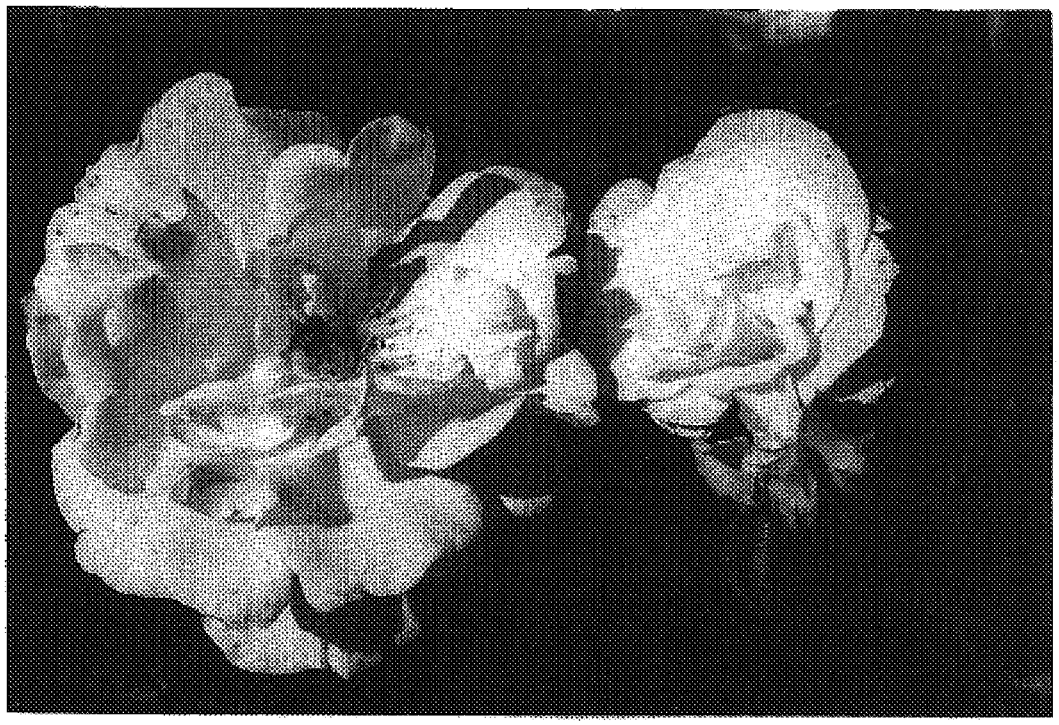
FIG. 2 illustrates at the right a typical fully open flower and at the left a fully mature flower immediately prior to petal drop.
Figure 3:
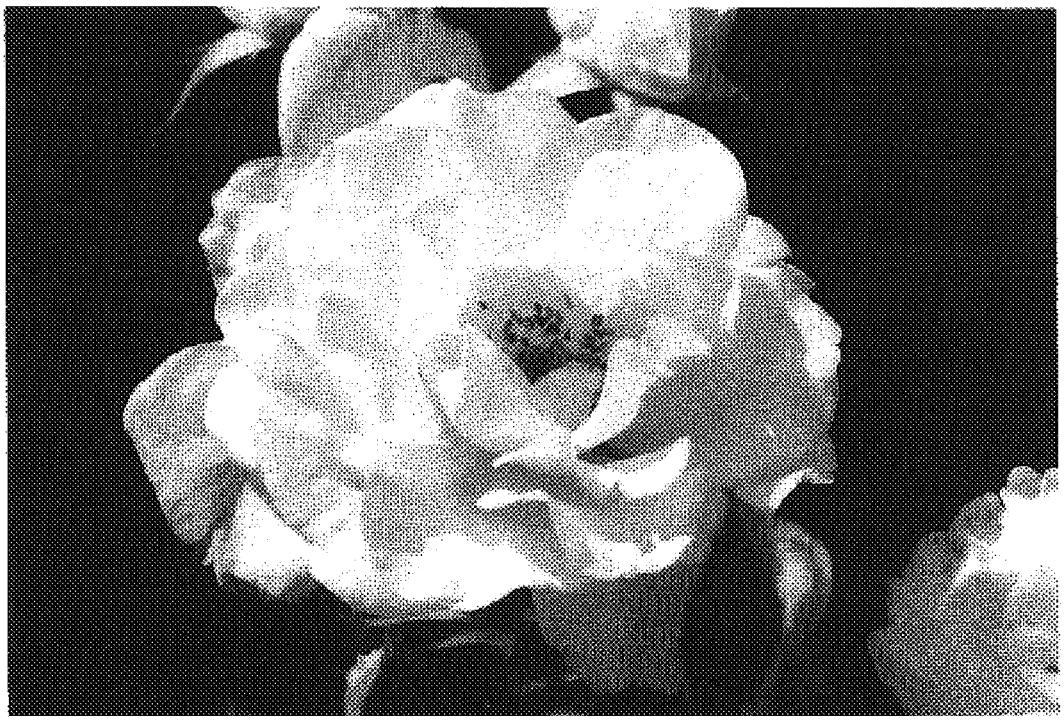
FIG. 3 illustrates a close view of another typical mature flower.

Branches:
- *Color*.—Young stems: Yellow-Green Group 146C suffused with Greyed-Purple Group 183B. Adult wood: Yellow-Green Group 147B with streaks of Grey-Brown Group 199B.
- *Texture*.—Young stems are glabrous and adult wood is rough with bark-like ridges.
- *Thorns*.—Size: approximately 1.5 cm in length on average. See the thorns on the new growth in FIG. 1. Color: Yellow-Green Group 146D suffused with Greyed-Purple Group 185B. Shape: generally triangular to slightly hooked. Quantity: approximately 4 on average over a length of 5 cm.

Leaves:
- *Stipules*.—Generally parallel with a long and pointed auricle facing outward, the shape ranges from narrow to triangular, approximately 2.3 cm in length on average, approximately 4.5 mm in width on average, the color of the upper surface is near Yellow-Green Group 146C with some Yellow-Green Group 146B on ridges on both sides of the central ridge, and the color of the under surface is Yellow-Green Group 146C.
- *Petioles*.—Upper surface: Yellow-Green Group 146B suffused with Greyed-Purple Group 185B. Under surface: Yellow-Green Group 146D. Length: approximately 2.9 cm on average. Texture: generally glabrous and tomentose on the upper side to varying degrees.
- *Size*.—Approximately 10.1 cm in length and width for a five-leaflet leaf.
- *Leaflets*.—Number: 3, 5 (most often), and 7. Shape: generally ovate with a rounded base and an acuminate tip. Margin: serrulate. Texture: bears a semi-glossy finish. Length: approximately 4.75 cm on average. Width: approximately 3.5 cm on average. General appearance: medium green with a semi-glossy surface when mature. Color (young foliage): Upper surface: between Yellow-Green Group 146A and 147A and blended with Greyed-Purple Group 187A and Greyed-Purple Group 187B towards the margin. Under surface: Yellow-Green Group 146A suffused at the margin with Greyed-Purple Group 187B. Color (adult foliage): Upper surface: between Yellow-Green Group 146A and 147A with some leaflets comonly retaining Greyed-Purple Group 187B at the margin. Under surface: Yellow-Green Group 147A commonly with some streaking of Greyed-Purple Group 187B.

Inflorescence:
- *Number of flowers*.—Commonly aproximately 5 blooms in a cluster on average per lateral stem.
- *Peduncle*.—Between Yellow-Green Group 144B and 144C, moderate to strong in strength, and glabrous with a few short spines.
- *Sepals*.—Upper surface: between Yellow-Green Group 144A and Yellow-Green Group 145C and commonly blended with Red-Purple Group 59A at the margin. Under surface: Yellow-Green Group 146B with some Yellow-Green Group 144B and blended with Red-Purple Group 59A at the center. Size: Approximately 4 cm in length on average. Shape: sharply pointed tip and a truncate base, upright in the bud stage, generally horizontal when opening, and reflexed at full bloom. Texture: Tomentose on the upper surface and strigose with short hairs on the under surface. Foliaceous appendages: commonly present on three outer sepals with one or two appendages per side, approximately 5.0 mm in length on average with a pointed apex and a ciliate margin.
- *Buds*.—Shape: slender to urn-shaped. Size: medium. Length: approximately 1.75 cm on average. Diameter: Approximately 2.5 cm on average. Color: Upper petal surface: Yellow Group 12A. Under petal surface: Yellow Group 10A.
- *Flower*.—Arrangement in a cluster or cyme. Diameter: approximately 5 cm on average. Form: double. Color (when opening begins): Upper surface: Yellow Group 10C blending to Yellow Group 9A towards the basal petal spot. Under surface: Yellow Group 10C blending to Yellow Group 10A towards the basal petal spot. Color (when blooming): Upper surface: Yellow Group 9D. Under surface: Yellow Group 9D suffused with Yellow Group 9B towards the basal petal spot. Color (at end of blooming): Upper surface: Yellow Group 11D. Under surface: Yellow Group 11D suffused with Yellow Group 9C and 9D. Color (basal petal spot): Yellow Group 9D.

Fragrance: medium rose. Lasting quality: the blossoms commonly last approximately 4 to 6 days on average depending upon the temperature and sunlight exposure. Petal number: commonly approximately 32 on average under normal growing conditons. Petal shape: wedge-shaped commonly with a slightly curled apex. Petal size: approximately 3.8 cm in length on average, and approximately 3.2 cm in width on average. Petal texture: glabrous, smooth and glossy. Petal drop: commonly the petals detach cleanly at full blossom maturity. Anther color: Yellow Group 13A in coloration. Anther size: approximately 3.0 mm in length on average, and approximately 1.8 mm in width on average. Pollen color: Yellow Group 14B. Filament number: commonly approximately 84 on average. Filament length: approximately 8.2 mm on average. Filament color: Yellow-Orange Group 14C. Pistils: approximately 52 on average, and are separate and free. Stigma color: Yellow-Orange Group 15B in coloration. Stigma size: approximately 1.0 mm in length on average, and approximately 0.5 mm in diameter on average. Style color: Yellow-Green Group 154C in coloration. Style length: approximately 6.5 mm on average. Receptacle: when the flower is fully opened urn-shaped, approximately 7.2 mm in length on average, approximately 9.1 mm in diameter on average, commonly between Yellow-Green Group 144B and 144C in coloration with some coloration of Greyed-Purple Group 184A on the side exposed to the sun, and generally glabrous with some glaucous covering. Hips: ellipsoid in configuration, glabrous with some ridges, approximately 1.5 cm in length, approximately 1.25 cm in width, and between Yellow-Green Group 144A and 144B with some splotches of Greyed-Red Group 183C and 183D in coloration. Seeds: light beige in coloration and approximately 4 mm in length.

Development:

*Vegetation*.—Vigorous and dense.

*Blooming*.—Recurrently throughout the season.

*Resistance to diseases*.—Highly tolerant to Black Spot, and Powdery Mildew.

*Hardiness zone*.—U.S.D.A. Hardiness Zone Nos. 4 to 9.

What is claimed is:

1. A new and distinct variety of landscape shrub rose plant characterized by the following combination of characteristics:

(a) exhibits a dense upright and bushy growth habit, (b) forms on a recurrent basis in clusters attractive double lemon yellow blossoms that mature to pale yellow creating a blend of yellow tints, (c) forms attractive semi-glossy medium green foliage, (d) is highly tolerant to Black Spot and Powdery Mildew, and (e) is particularly well suited for growing as attractive ornamentation in parks and gardens;

substantially as herein shown and described.

* * * * *